(12) United States Patent
Martikka et al.

(10) Patent No.: US 10,568,549 B2
(45) Date of Patent: Feb. 25, 2020

(54) WEARABLE ACTIVITY MONITORING DEVICE AND RELATED METHOD

(71) Applicant: Suunto Oy, Vantaa (FI)

(72) Inventors: Mikko Martikka, Vantaa (FI); Erik Lindman, Vantaa (FI)

(73) Assignee: Amer Sports Digital Services Oy, Vantaa (FI)

( * ) Notice: Subject to any disclaimer, the term of this patent is extended or adjusted under 35 U.S.C. 154(b) by 0 days.

(21) Appl. No.: 15/473,667

(22) Filed: Mar. 30, 2017

(65) Prior Publication Data

US 2017/0202486 A1 Jul. 20, 2017

Related U.S. Application Data

(63) Continuation-in-part of application No. 14/331,268, filed on Jul. 15, 2014.

(30) Foreign Application Priority Data

Jul. 11, 2014 (FI) ...................................... 20145671

(51) Int. Cl.
*A61B 5/11* (2006.01)
*A61B 5/0205* (2006.01)
(Continued)

(52) U.S. Cl.
CPC .......... *A61B 5/1118* (2013.01); *A61B 5/0205* (2013.01); *A61B 5/02416* (2013.01);
(Continued)

(58) Field of Classification Search
CPC ...... A61B 5/4528; A61B 5/1071; A61B 5/103
(Continued)

(56) References Cited

U.S. PATENT DOCUMENTS 5,989,200 A  11/1999  Yoshimura et al.
7,328,612 B2  2/2008  Jamsen et al.
(Continued)

FOREIGN PATENT DOCUMENTS

DE  102010048763 A1  4/2012
EP  2505238 A1  10/2012
(Continued)

*Primary Examiner* — Daniel L Cerioni
(74) *Attorney, Agent, or Firm* — Seppo Laine Oy (57) ABSTRACT

The invention relates to wearable electronic devices for monitoring physical activities of a person. The invention also concerns related methods and computer program products. According to the invention, a first sensor for measuring acceleration data and a second sensor for measuring heart rate data is provided. A data processing unit is configured to operate in a first mode when data is read from said first and second sensors and in a second mode when data is not read from at least one of said first and second sensors. In the first operating mode the processing unit cumulatively computes and updates a heart rate offset value based on at least one of the following data: a predetermined pulse of the person a rest, a predetermined fitness level of the person, a current recovery pulse of the person, and/or the cumulated acceleration data during the current activity. It also computes a current activity gain value based on acceleration data and heart beat rate data. The data processing unit is further configured to compute an estimate of the heart beat rate based on said offset value and said gain value during said second operating mode.

31 Claims, 7 Drawing Sheets

(51) Int. Cl.
*A61B 5/00* (2006.01)
*A61B 5/024* (2006.01)

(52) U.S. Cl.
CPC .......... *A61B 5/02438* (2013.01); *A61B 5/112* (2013.01); *A61B 5/1123* (2013.01); *A61B 5/4866* (2013.01); *A61B 5/681* (2013.01); *A61B 5/7246* (2013.01); *A61B 5/0022* (2013.01); *A61B 5/7275* (2013.01); *A61B 2562/0219* (2013.01)

(58) Field of Classification Search
USPC .......................................................... 600/595
See application file for complete search history.

(56) References Cited

U.S. PATENT DOCUMENTS

| | | |
|---|---|---|
| 2005/0172311 A1 | 8/2005 | Hjelt |
| 2007/0051369 A1* | 3/2007 | Choi .................. A61B 5/02438 128/204.21 |
| 2007/0208544 A1 | 9/2007 | Kulach et al. |
| 2008/0275348 A1 | 11/2008 | Catt |
| 2009/0043531 A1 | 2/2009 | Kahn |
| 2009/0163835 A1 | 6/2009 | Logan et al. |
| 2010/0010774 A1 | 1/2010 | Ma et al. |
| 2010/0185125 A1 | 7/2010 | Damen |
| 2011/0263993 A1 | 10/2011 | Martikka et al. |
| 2012/0203077 A1* | 8/2012 | He ..................... A61B 5/02055 600/301 |
| 2012/0253486 A1 | 10/2012 | Niemimäki |
| 2013/0090881 A1 | 4/2013 | Janardhanan et al. |
| 2013/0173174 A1 | 7/2013 | Baxi |
| 2013/0179110 A1 | 7/2013 | Lee |
| 2013/0191069 A1 | 7/2013 | Ravindran |
| 2013/0274587 A1 | 10/2013 | Coza |
| 2013/0325396 A1 | 12/2013 | Yuen et al. |
| 2014/0180033 A1* | 6/2014 | Altini .................... A61B 5/1118 600/301 |
| 2015/0099945 A1 | 4/2015 | Hawkins |
| 2015/0120018 A1 | 4/2015 | Wisbey et al. |
| 2015/0374240 A1* | 12/2015 | Lee ..................... A61B 5/0205 600/483 |
| 2016/0007888 A1* | 1/2016 | Nieminen ............. A61B 5/1118 600/595 |
| 2016/0143579 A1* | 5/2016 | Martikka ............... A61B 5/486 600/301 |
| 2016/0374566 A1* | 12/2016 | Fung .................... A61B 5/0205 600/483 |

FOREIGN PATENT DOCUMENTS

| | | | |
|---|---|---|---|
| EP | 2654030 A1 | 10/2013 | |
| WO | WO 2007102134 A2 | 9/2007 | |
| WO | WO 2009021147 A1 | 2/2009 | |
| WO | WO 2012170305 A1 | 12/2012 | |
| WO | WO 2015058923 A1 * | 4/2015 | ........... A61B 5/7264 |

* cited by examiner

WEARABLE ACTIVITY MONITORING DEVICE AND RELATED METHOD

FIELD OF THE INVENTION

The invention relates to wearable electronic devices for monitoring physical activities of a person. The invention also concerns related methods and computer program products.

BACKGROUND OF THE INVENTION

Wearable activity monitoring devices, so-called "activity trackers" are intended to determine overall activity of a person during his/her daily duties and have become popular lately. There are devices utilizing heart rate measurement, acceleration measurement and satellite positioning systems. Some devices utilize only internal sensors, some receive data from external modules, such as foot pods, heart rate sensors or positioning pods. There are devices that are provided in the form of modules attachable to a chest band or other piece of garment or body part. One class of devices is provided in the form of wristbands (so-called "activity bracelets)" with integral accelerometer for measurement of movements of the users wrist during his or her daily activities and determination of an activity index, which is presented to the user. The activity tracking can also be implemented as a function in a multifunction digital wrist watch, wristop computer or other mobile device, such as a mobile phone.

In particular for people aiming at serious activity tracking for the purposes of fitness monitoring or body weight control, the activity indices given by the existing devices, in particular those based on acceleration only, are often too inaccurate or inconsistent between different usage periods. There is a particular difficulty in determining activity using acceleration sensors located on the wrist of the user, because wrist movement can relate either to ordinary lightweight daily tasks or hard-intensity training, or anything between these extremes. Therefore, as concerns the real physiological effect of the activities done, either too little or too much activity may be registered.

For obtaining a better estimate of real activity, one can try to detect which kind of exercise the user is carrying out. U.S. Pat. No. 7,328,612 discloses a method and apparatus for detecting types of exercise from an acceleration signal using at least two different characteristics computed from the acceleration signal and comparison tables for the characteristics stored in the memory of the apparatus. The method is particularly designed for acceleration signal measured at a lower limb of a person and is not expected to provide equally reliable results for wrist-based measurements, because wrist movement is only loosely related to feet movements. U.S. Pat. No. 5,989,200 disclose a method which computes and utilizes an average of peak accelerations caused by steps.

Measuring and computing a heart rate value is in most cases done continuously, and the measured heart rate data especially when put in context of the activity executed, yields much useful information for analyzing the performance and the abilities of the user of such a device. However, continuous measuring, signaling and computing represents both a technical and a user-experience-related problem of the presently available activity trackers, which the short battery life. This is particularly a problem with optical sensors collecting physiological data, such as the heart rate, from the human body. Thus, there is a need for improved activity tracking devices and methods.

SUMMARY OF THE INVENTION

It is an aim of the invention to provide a novel activity monitoring device overcoming at least some of the above-mentioned problems and in particular being capable of giving augmented and physiologically more accurate activity estimates, while providing a considerable longer battery life than usually is the case. A further aim is to provide a corresponding activity monitoring method and software product.

According to a first aspect, the invention provides a device for monitoring physical activity of a person, comprising at least one first sensor for measuring acceleration data relating to movements of said person, at least one second sensor for measuring heart rate data corresponding to the heart beat rate of said person, a data processing unit comprising at least one processing core, at least one memory unit including computer program code, the at least one memory unit and the computer program code being configured to, with the at least one processing core, cause the apparatus to operate in a first mode when data is read from said first and second sensors and in a second mode when data is not read from at least one of said first and second sensors, and where the processing unit in said first operating mode:

cumulatively computes and updates a heart rate offset value based on at least one of the following data: a predetermined pulse of the person a rest, a predetermined fitness level of the person, a current recovery pulse of the person, and/or the cumulated acceleration data during the current activity, computes a current activity gain value based on acceleration data and heart beat rate data, and wherein said data processing unit being further configured to compute an estimate of the heart beat rate based on said offset value and said gain value during said second operating mode.

According to one embodiment, the device comprises at least first and second sensors and a memory unit as described above, and the data processing unit is configured to calculate the heart beat rate offset value as a parameter corresponding to a recovery time of the user, said recovery time being computed as a function of the duration of the current activity, a predetermined or estimated heart beat rate or pulse value characteristic of the user at rest, and the current heart rate.

According to a third embodiment, the device comprises at least first and second sensors as described above and the data processing unit is configured to calculate the current gain value as a parameter corresponding to the ratio of the differences between said heart beat rate data and said acceleration data.

According to further embodiments, the data processing unit in configured to display the current estimated heart beat rate value based on said offset value and said gain value during said second operating mode on a user-readable a display unit of said device. Alternatively or in addition, the processing unit may be configured to store in said at least one memory unit the estimated heart beat rate values based on said offset value and said gain value during said second operating mode. With the use of a memory in connection with a display, it is possible to graphically show how the heart rate values are developing over time, for example.

According to further embodiments the data processing unit in configured to switch between said first and second operating modes with predefined intervals. For example, the processing unit may be operating in said second operating mode at least 5 times longer than in said first operating mode, in one embodiment the duration of the first operating mode is one minute and the duration of the second operating mode is 9 minutes. In this way, considerable less battery power is needed to compute and display reliable heart rate values, compared to measuring and displaying them constantly.

According to further embodiments of the invention, the data processing unit in configured to
- detect periodic motions from measured acceleration data,
- determine frequency of the periodic motions,
- determine whether the frequency of the periodic motions is at a predefined frequency range, and to
- compute a new current activity gain value using said frequency of periodic motions if the frequency of the periodic motions is at said predefined frequency range.

For example, in this way only activities related to the execution of a certain sport may be recorded, while intermittent pauses or other diverse activities are filtered out.

The data processing unit may further comprise means for determining determine an average acceleration value from acceleration data measured during said first operating mode, to determine whether said average acceleration is within a predefined acceleration range, and to compute a new current activity gain value using said average acceleration if the average acceleration is within said predefined acceleration range. In certain embodiments, at least first and second average acceleration values are determined from acceleration data measured during at least two time periods during said first operating mode, Then at least first and second average heart beat rate values are determined from heart rate beat data measured during at least two time periods during said first operating mode, Finally, a new current activity gain value is computed, based on the ratio between the differences ($\Delta HR/\Delta acc$) of said at least two average heart beat rate and acceleration values.

Further embodiments of the inventive device includes that the processing unit is configured to computing estimates of said offset value and said gain value during said second operating mode by linear extrapolation of earlier measured values during the first operating mode, and to use at least one of the following parameters stored in said memory unit for computing and updating said offset value: age of the person, sex of the person, mass of the person, fitness index of the person, maximum oxygen intake value ($VO_{2,max}$) of the person.

The inventive device may have means for mounting the device on the wrist of the person, and/or it may be a wearable computer comprising means for wireless reception of data from the at least one first and second sensors. The second sensor may comprise an optical heart rate sensor.

As a second aspect of the invention, an inventive method is provided for monitoring physical activity of a person by operating a monitoring device in a first operating mode and in a second operating mode. The method comprises the steps of:
- measuring in said first operating mode acceleration data relating to movements of said person with a first sensor into a processing unit,
- measuring in said first operating mode heart rate data corresponding to the heart beat rate of said person with a second sensor into said processing unit,
- computing and updating a cumulative heart rate offset value based on at least one of the following data: a predetermined pulse of the person a rest, a predetermined fitness level of the person, a current recovery pulse of the person, and/or the cumulated acceleration data during the current activity,
- computing a current activity gain value based on acceleration data and heart beat rate data, and
- computing an estimate of the heart beat rate based on said offset value and said gain value during said second operating mode.

According to some embodiments, the second sensor measuring the heart rate comprises an optical heart rate sensor. If a heart rate signal from said optical sensor is unavailable, the monitoring device may then be maintained in the second operating mode longer than the predefined interval.

A third aspect of the invention includes a computer program product for monitoring physical activity of a person stored on a computer readable non-transitory storage medium in a monitoring device, said product comprising a computer readable program code causing said monitoring device to operate in a first operating mode and in a second operating mode, wherein:
- in said first operating mode acceleration data relating to movements of said person is measured with a first sensor into a processing unit,
- in said first operating mode heart rate data corresponding to the heart beat rate of said person is measured with a second sensor into said processing unit,
- a cumulative heart rate offset value is computed and updated based on at least one of the following data: a predetermined pulse of the person a rest, a predetermined fitness level of the person, a current recovery pulse of the person, and/or the cumulated acceleration data during the current activity,
- a current activity gain value is computed based on acceleration data and heart beat rate data, and
- an estimate of the heart beat rate is computed based on said offset value and said gain value during said second operating mode.

More specifically, the invention is characterized by what is stated in the independent claims.

The invention provides considerable advantages. The invention provides an efficient activity monitoring device that can operate "in the background", without the need of the user to specifically switch to a training mode. The present device may concentrate on detecting and recording all activities which are most common everyday exercises that are beneficial for individuals. They typically form a major portion of physical performances of an average person that has a positive effect on the fitness of the person, in addition to specific training sessions the person is doing (e.g. gym training or team sports). E.g. walking and running can be reliably distinguished from other activities by means of embodiments of the invention and the physical intensity, i.e., load for the body, of walking and running can be reliably determined using the acceleration data measured from wrist. Thus, a very reliable estimate on the effect of these activities on the metabolic system of a person is obtained.

In particular, the present device may be configured to detect and record at least walking and running activity in the activity monitoring mode. Walking typically forms a majority of everyday activities that are beneficial for health and the cumulative amount of walking in the form of the activity index is therefore of particular interest to many users. Running for short distances outside actual running sessions is not uncommon and recording thereof according to embodiments of the invention provides additional advantages.

For other training sessions, the user may be given the option to record activity in one or more separate training modes, potentially utilizing also more than one acceleration sensor.

In a preferred embodiment, the present device is a multifunction digital wrist watch or wristop computer, having the present activity monitoring implemented as one function thereof. If desired, the monitoring may in principle take place "24/7", i.e. essentially all times the device is worn, or at least during daytime.

The present device reads data from the first and second sensors intermittently with a predefined interval in the activity monitoring mode. This saves a considerable amount of battery energy compared with for example the continuous use of a wired or wireless acceleration sensor and a heart rate sensor.

The present device is preferably a wrist-worn device. Compared with other wearable devices and mobile phones having acceleration and other sensing capabilities, the present device has a power consumption advantage. It is not desirable to run additional energy-consuming measurement and computing operations in e.g. mobile phones, whose operating times are low even without such operations. A mobile phone is also often left on a table, for example, whereby the person's activity is not recorded.

Compared with devices using satellite positioning to determine overall activity, the present invention has considerably lower energy consumption and also works indoors.

The dependent claims are focused on selected embodiments of the invention.

The abovementioned embodiments and those that will be described later or claimed can be combined with each other and with the different aspects of the invention.

The term "activity index" refers to any parameter value which is derived from physical movements or conditions of the person by means of measuring, for example, acceleration data or heart beat rate data of the person, and processing this data in a computing unit in accordance with the invention. The activity index may according to the invention be cumulative, i.e. its value being continuously updated, or current, whereby it describes the momentaneous amount of motoric or metabolic activity of the person. The activity index can be reset for example automatically on a daily basis, or in response to a user command. The activity index can be a dimensionless quantity or one with a dimension. In particular, it can show a relative intensity. It is also possible to compute other parameters, such as energy consumption or time needed for full recovery from preceding physical performances (recovery time), based on the activity index. The activity index can also itself represent energy consumption or recovery time. Energy consumption has an established meaning in the art, whereas the concept of recovery time and one exemplary method for calculation thereof is described in US 2011/263993.

"Recording activity" means updating the activity index using a measurement and computing process in accordance with the invention.

"Activity monitoring mode" is an operating mode of the data processing unit of the device in which a certain acceleration measurement rules and acceleration data processing algorithms are used to record activity. The invention focuses on the implementation of computing and updating a cumulative heart rate offset value based at least on previously stored heart rate data and/or cumulated acceleration data, and on computing a current activity gain value based on current acceleration and heart rate data.

"Walking-related movements" of a person mean body movements (in particular wrist movements when a wrist-worn device is used) that are associated with normal human gait at the pace of walking (which is typically less than 6 km/h). In particular, "walking-related movements" are movements that produce acceleration data meeting predefined first criteria for magnitude and periodicity (frequency and stability of the frequency over a time period). Correspondingly, "running-related movements" mean movements that are associated with normal gait at the pace of running (typically 6 km/h or more). In particular, "running-related movements" are movements that produce acceleration data meeting predefined second criteria for magnitude and periodicity, the second criteria being different from the first criteria. The second criteria can be applied after application of the first criteria, thus prioritizing the detection of walking.

Next, embodiments and advantages of the invention are described in more detail with reference to the attached drawings.

DETAILED DESCRIPTION OF EMBODIMENTS

Figure 1:
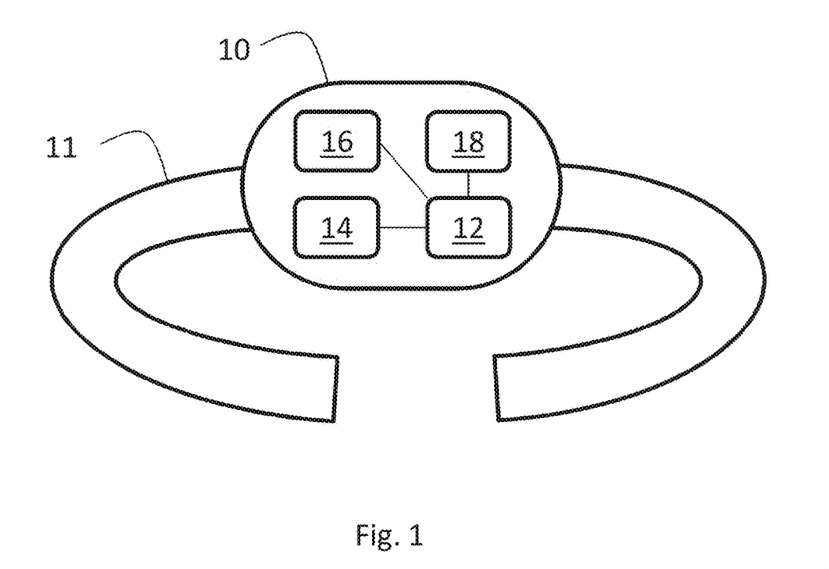
FIG. 1 shows a schematic view of a device according to the invention.

FIG. 1 shows a device according to one embodiment the invention. The device comprises a main unit 10 and a wristband 11 attached to the main unit 10. The main unit comprises a data processing unit 12 and an acceleration sensor 14, memory unit 16 and user interface unit 18 functionally connected to the data processing unit 12. The data processing unit 12 can comprise a microcontroller, optionally with the memory unit 16 built therein. The data processing unit 12 is capable of running a program code including instructions necessary for the device to operate according to the invention.

The acceleration sensor 14 can comprise a one-, two- or most preferably a three-dimensional accelerometer, which are well known in the art.

The user interface unit 18 herein comprises the necessary means for the user to interact with the program code of the device, e.g. switch on and off the device, to change mode of activity monitoring mode of the device or to input personal parameters (input means) and optionally to visually inspect the determined activity index (output means). The input means may comprise one or more buttons or a touchscreen. The output means may comprise a display of any kind. According to one embodiment, either the input means, output means or both are implemented as a contact-based or wireless communication means allowing the user to interact with the device using another device, such as mobile phone or computer, over a communication link.

Figure 2:
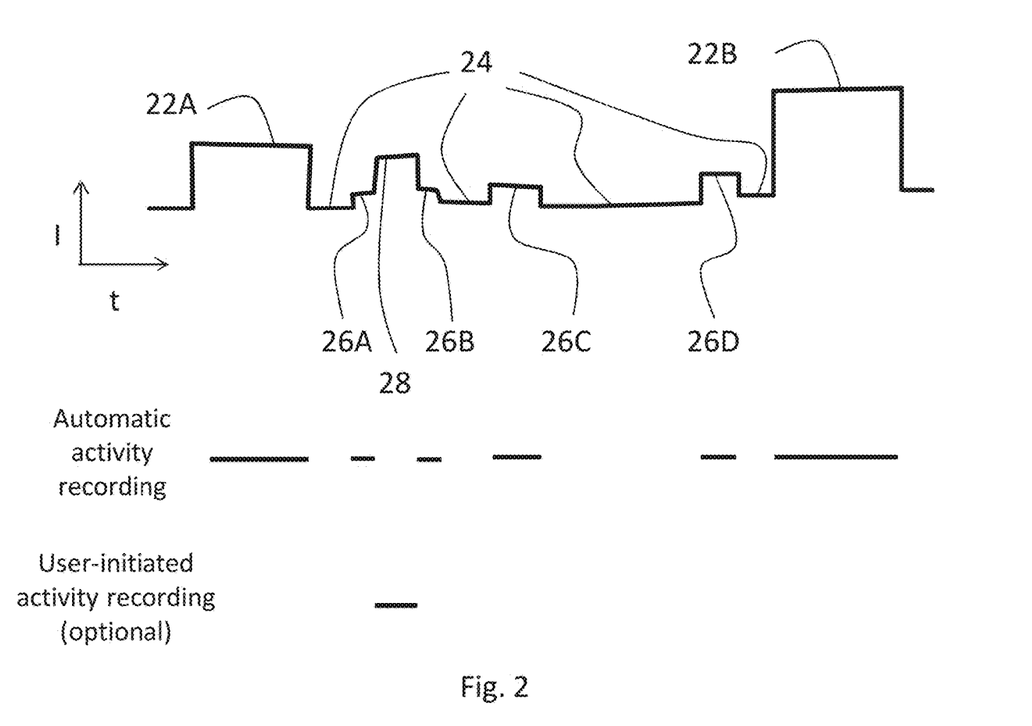
FIG. 2 shows an exemplary graph of intensity of a person's activities over time, as well as periods of automatic and optional user-initiated activity recording using a device according to the invention.

FIG. 2 shows a graph illustrating the operation of the device in an automatic activity determination mode during an exemplary time period, including different types of activities of a person that cause the person's metabolic activity to temporarily rise over a metabolic base rate. Intensity periods 22A and 22B represent running performances (for example running in the morning to a workplace and in the afternoon back to home). Intensity periods 26A-D represent walking performances during the workday. Intensity period 28 represents a non-walking and non-running performance (such as a gym training session), preceded and followed by short walks 26A and 26B (to the gym and back). Intermediate periods 24 represent everything else the person in doing during the day (such as ordinary office work with metabolic activity close to metabolic base rate).

As illustrated, the automatic activity determination is designed to detect and record activity during the running and walking periods 22A-B and 26A-D, but not during the gym (or some other sports) period 28. If the activity during the gym period is to be recorded, the device may be provided with another mode of operation which the user initiates through the interface unit of the device. This second mode of operation ("second activity monitoring mode", discussed later in more detail) is typically not based on cadence detection and determination of the intensity of activity based on cadence, but some other algorithm better reflecting the intensity of the particular exercise into the activity index.

There may be a common activity index for all types of activities recorded, or two or more separate activity indices, which are updated separately depending on the activity monitoring mode concerned.

Figure 3A:
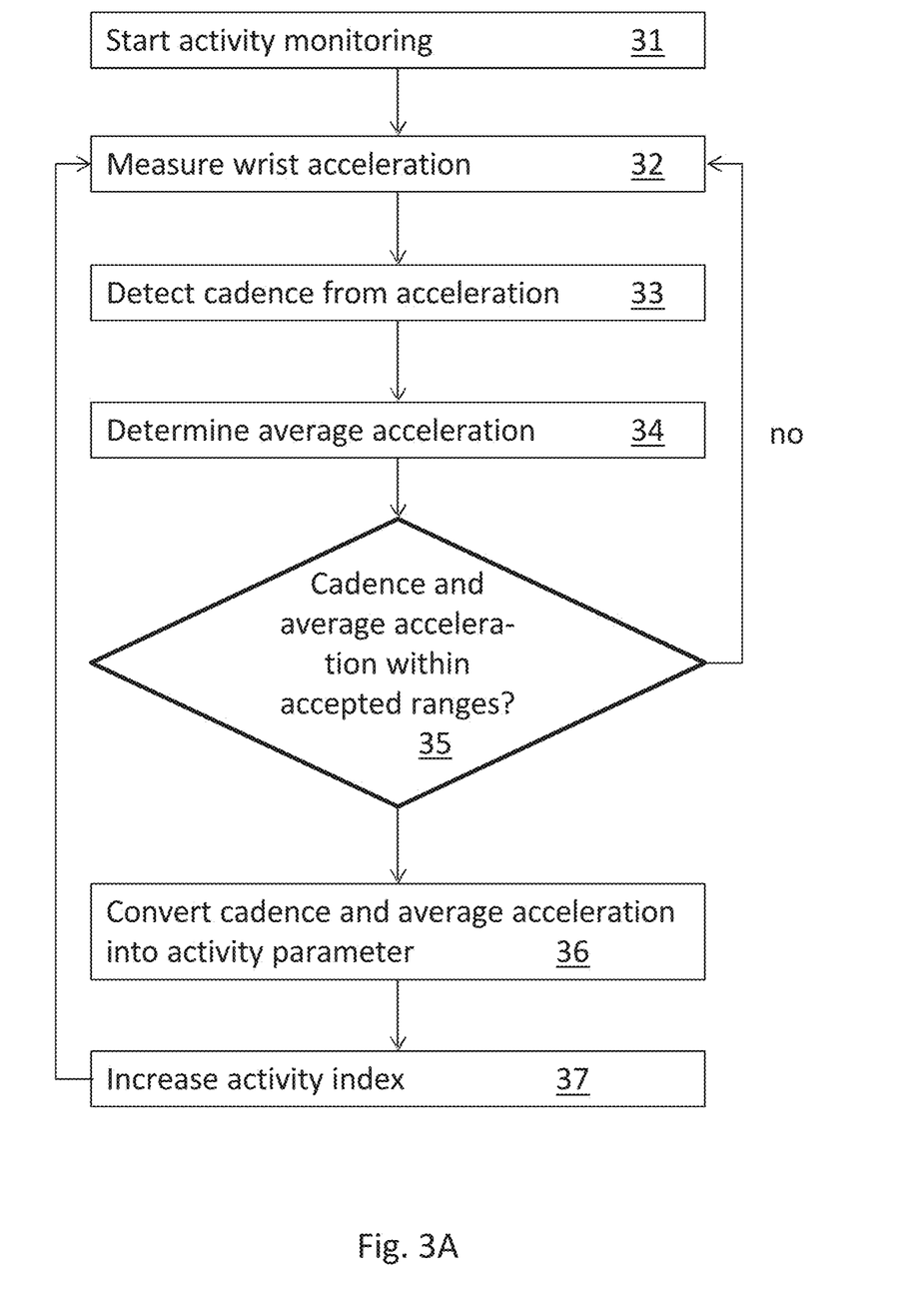
FIGS. 3A and 3B show flow charts of the method according to selected embodiments of the invention.

Explaining now in more detail a practical implementation of the automatic activity monitoring mode of the device, FIG. 3A shows a flow chart including main steps of the present method according to one embodiment. Activity monitoring in the automatic mode is started in step 31. This may occur by turning on the device or in response to a separate user action through the user interface. Then the device starts measuring acceleration continuously in step 32 (measurement continues preferably in the background although herein illustrated as a single step for simplicity). The acceleration signal is analyzed in step 33 in the data processing unit in order to detect cadence of the person. This is discussed in detail below. The acceleration signal is also used to calculate the average acceleration over a predefined time period. Then, if cadence is detected in the first place, it is checked in step 35 whether the cadence and average acceleration are within predefined cadence and acceleration ranges which are indicative of walking and/or running. In the negative case, the steps 32-35 are repeated. In the affirmative case, the cadence and average acceleration are used to compute a parameter which is descriptive of the intensity of the walking or running activity which is going on (step 36), and the activity index value is increased accordingly (step 37). Then, the process returns to step 32.

Cadence can be determined in the data processing unit by investigating the periodically repeating features, such as acceleration peaks, in the acceleration signal. According to one embodiment, the features being repeated are detected and their time stamps are recorded. The frequency and regularity, i.e. periodicity, of the features can be determined from the time stamps. If the frequency if too low or too high or the features do not occur regularly enough, the peaks do not represent cadence originating from walking or running. Predefined criteria for the allowed frequency and regularity ranges can be used. Regularity can be assessed for example by calculating correlation between intervals between successive time stamps. The correlation factor must exceed a predefined threshold correlation factor value. Such correlation analysis can be implemented in a wearable device efficiently in the time domain.

In an alternative embodiment, cadence is determined in the data processing unit using Fourier analysis for the acceleration data signal to determine its periodic components. High enough presence of periodic components in a predefined frequency range is an indication of walking or running. Discrete Fourier analysis can also be relatively efficiently implemented in a wearable device.

Figure 3B:
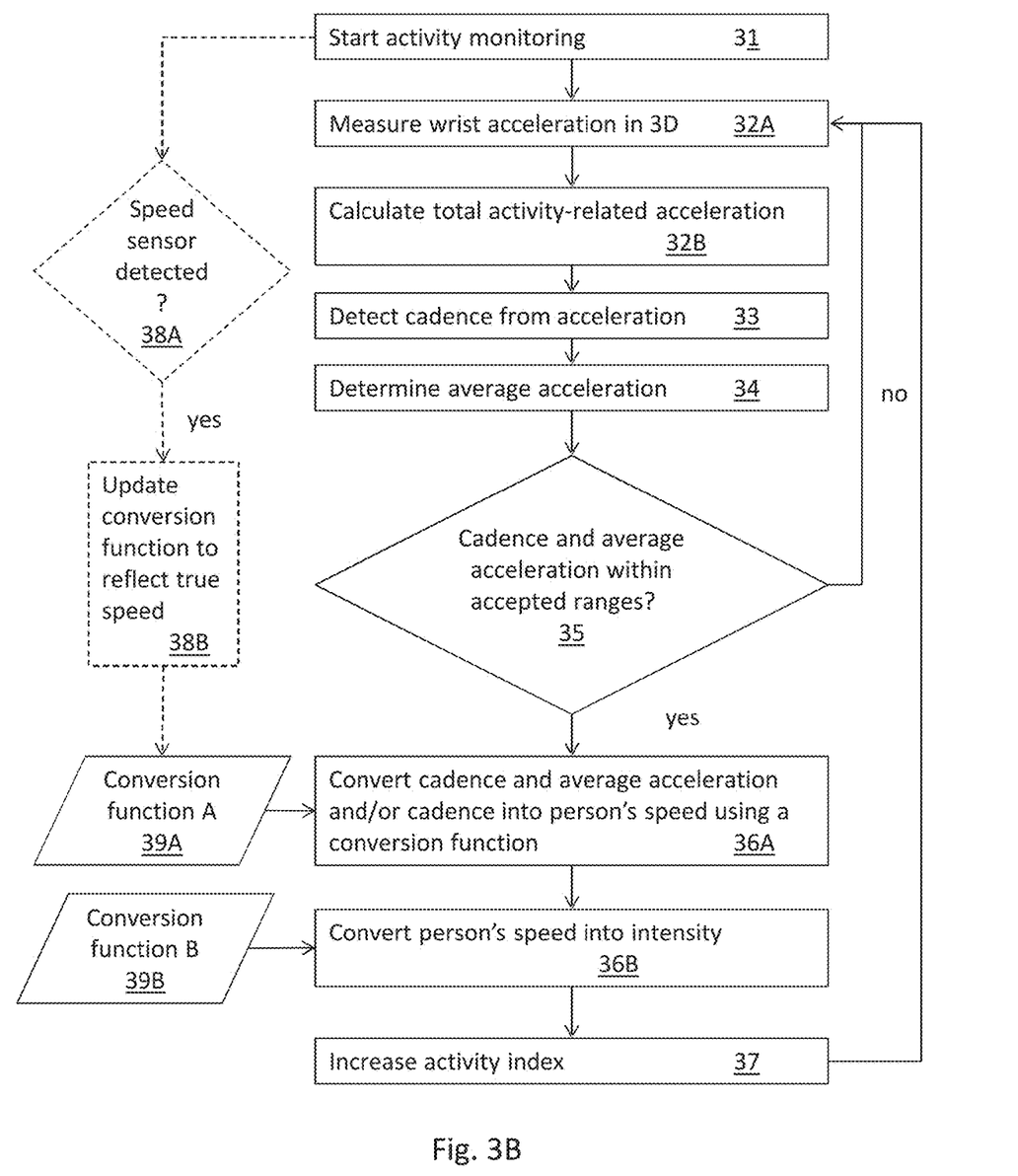
Figure 3C:
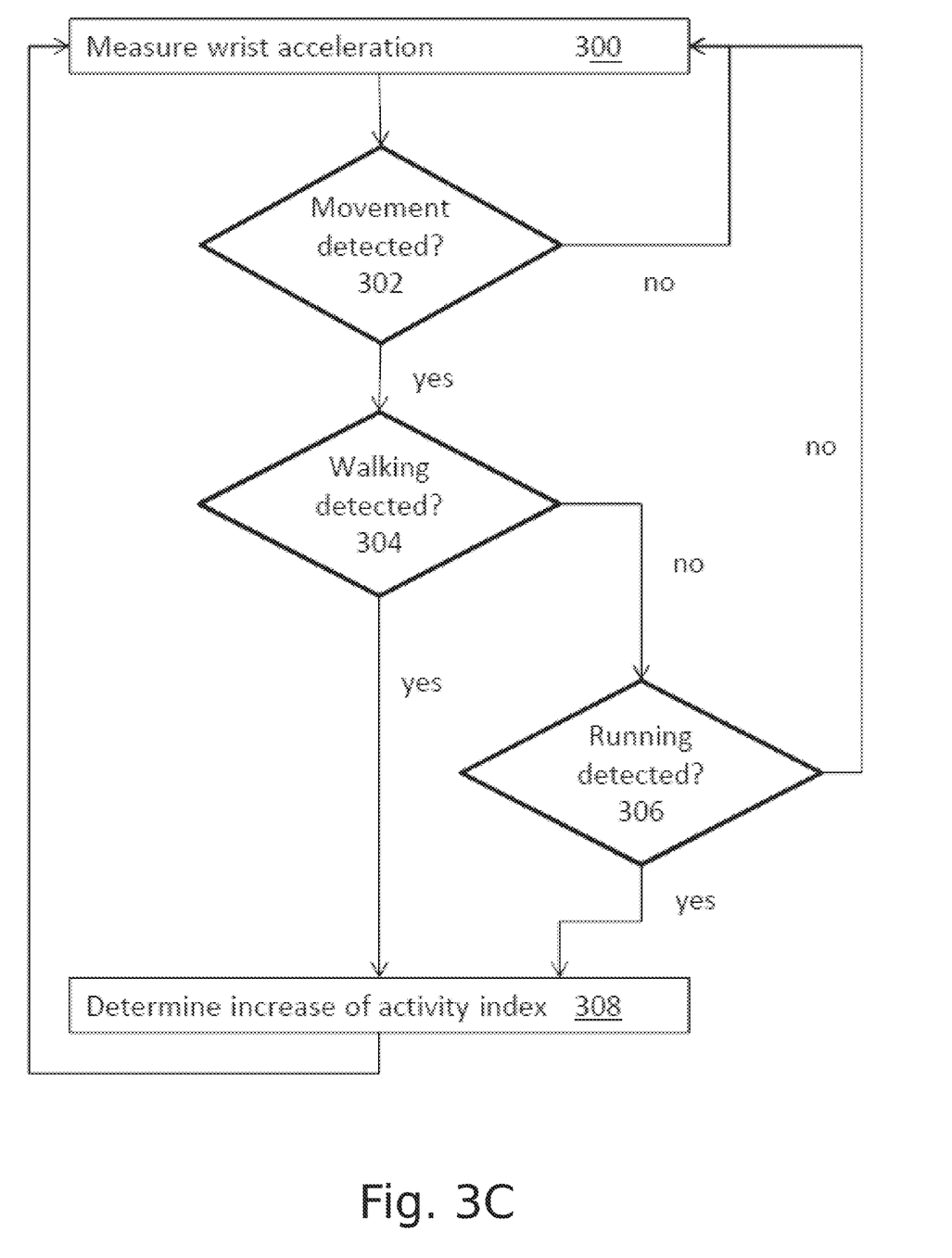
FIG. 3C shows a flow chart of the implementation of the invention according to one embodiment.

FIG. 3C illustrates one embodiment of the invention, starting with measurement of wrist acceleration in step 300. The processing unit is configured to first determine (step 302) whether said acceleration data exceeds a predefined magnitude threshold (e.g. the instant magnitude at the moment of measurement or the average magnitude over a measurement period). Only if said acceleration data exceeds the predefined magnitude threshold, the processing unit continues to determine (step 304) whether the acceleration data corresponds to walking-related movements of the person using a first method and/or first criteria of detecting frequency of motions (cadence) from the acceleration data. Only if the acceleration data corresponds to walking-related movements of the person, the activity index value is updated (step 308) based on the acceleration data. In a further embodiment, if the acceleration data does not correspond to walking-related movements, the unit may be configured to determine (step 306) if the acceleration data corresponds to running-related movements of the person using a second method and/or second criteria of detecting cadence. Again, if the acceleration data corresponds to the running-related movements of the person, the activity index value is updated (step 308) based on the acceleration data. If the magnitude criteria and neither of the walking or running criteria is met, the activity index value is not updated. The described embodiments help to optimize the battery consumption of the device. It is computationally a relatively lightweight process to determine whether there is such acceleration that may originate from walking or running. Further, since there is typically more walking than running during an ordinary persons day, it is advantageous to check the walking criteria before the running criteria.

According to one embodiment, the cadence detection process comprises two parts: calculation of cadence of slow motions $c_{slow}$ and calculation of cadence of fast motions $c_{fast}$, $c_{slow}$ typically having higher priority. This means that the process returns the value of $c_{slow}$ if different from zero. If $c_{slow}$ is zero, the value of $c_{fast}$ is returned. The calculation of both $c_{slow}$ and $c_{fast}$ relies on detection of individual motions and checking if the motions repeat in cyclic manner. Otherwise, there is no cadence and a value is not returned at all. According to one embodiment the determination of $c_{slow}$ utilizes convolution for the detection of cyclicality. $c_{fast}$ may be implemented in a computationally more lightweight manner, using as the cyclicality criteria that n preceding time intervals between previous motions are within a predefined time window.

The slow motions referred to above can be in particular those corresponding to a first frequency (the frequency of walking), and the fast motions those corresponding to a second frequency (cadence) higher than that of the first frequency (the frequency of running).

FIG. 3B shows a preferred method in more detail, also including an optional autocalibration of acceleration-to-speed conversion carried in the method (dashed parts). The step 32 of FIG. 3A has been split into two sub-steps 32A and 32B, in which the acceleration is first measured in three dimensions to provide acceleration data separately for the three dimensions and then the total activity-related acceleration is computed based on the dimension-specific data. The activity related acceleration is obtained by computing the total magnitude of the acceleration vector, and optionally subtracting a gravity-based component from the acceleration data and/or filtering e.g. vibration- or noise-based components from the acceleration data.

The activity parameter determination step 36 has as well been split into two substeps 36A and 36B. In step 36A, the walking or running speed of the person is estimated based on the cadence and/or average acceleration data using a conversion function 39A (conversion function A) stored in the memory of the device. The conversion function 39A may be in the form of a mathematical formula, such as a piecewise linear function, or in table format, to mention some examples. The conversion function 39A uniquely binds average acceleration values to speed values. Preferably, the conversion function 39A has been determined taking the persons personal properties into account (such as running or walking style, affecting the average acceleration and/or cadence, and/or step length). For this purpose, an autocalibration method is described below, although manual calibration using user-input data is possible too. In step 36B, a relative intensity of the activity is determined based on the speed determined in step 36A. Again, a conversion function 39B (conversion function B) taking into account personal data of the user, is used. The personal data may comprise one or all of the following: age of the person, sex of the person, mass of the person, fitness index of the person, maximum oxygen intake value ($VO_{2,max}$) of the person. The conversion function may be a simple mathematical linear or non-linear formula taking the speed as input and using the personal data as weighing factors.

The autocalibration method referred to above for conversion function A utilizes a separate speed sensor, such as a satellite positioning sensor or foot pod, which gives a more reliable speed reading ("true" speed reading) than a purely wrist acceleration-based method, and is functionally connected to the present device. The connection may be a wired connection (e.g. a GPS receiver built-in in the device) or a wireless connection (e.g. a separate GPS receiver module or acceleration-based foot pod). If the device detects the presence of such sensor (step 38A), it uses a true speed reading provided by that sensor, for calibrating the conversion function 39A to reflect true dependency of speed on cadence and/or average acceleration. If the activity includes running and/or walking at practically all possible speeds, the whole conversion function becomes calibrated. The calibration can be done also piecewise, correcting only those parts of the conversion function that corresponds to the true speed readings available.

Autocalibration can be carried out when the device is in the first activity monitoring mode or in a second activity monitoring mode (e.g. a separate walking or running training mode specifically initiated by the user), which are discussed in more detail later. In particular, if a satellite positioning sensor is used as a reference in the autocalibration, the latter option is preferred because it ensures that the reference data originates from pure walking or running and not for example from movement during a boat trip. Thus, the possibility for incorrect calibrations is decreased.

According to one embodiment, the conversion step 36A is based solely on average acceleration-to-speed conversion. An example of this kind of conversion is given later in this document.

As concerns the accuracy of speed (and optionally distance) determination, and therefore the activity index, the cadence determination step 33, autocalibration step 39A and cadence check step 35 play an important role. This is mainly because wrist is a difficult location to be used for speed determination, if particular at slow speeds, and an error at these phases may result in other motions than those relating to walking and/or running are being recorded, which is not the aim in the automatic activity measurement mode.

It should be noted that in the automatic activity monitoring mode in the core of the present invention, the device is preferably adapted to only detect and record activities that fall into the categories of walking and/or running. If there is any other kind of activity taking place, even if producing a measurable acceleration signal, it is either left unrecorded or recorded in another activity monitoring mode initiated by the user manually. The walking and/or running activity detected is transformed into an activity index increase using the characteristics of the acceleration. In this way, the most common activities typically forming a major portion of all additional metabolism on top of baseline metabolism, are recorded very accurately in the background and without a need for the user to separately put the device into a training mode.

There are three preferred (and also sufficient) data processing steps, which allow for detection of walking and/or running. The first step is the reliable determination of cadence, i.e., periodic features of the acceleration signal occurring with sufficient regularity (corresponding to regularity of wrist movement during walking and/or running). The second step is checking that the cadence is at an allowed frequency range (corresponding to frequency of wrist movement during walking and/or running). The third step is checking that the average acceleration calculated based on the measured acceleration data is at an allowed acceleration range (corresponding to possible wrist movement during walking and/or running). All these steps have been discussed above in detail, and can be carried out in practice in different ways and in various stages of data processing. According to a preferred embodiment, all these checks are carried out, making the detection very robust.

According to one embodiment, walking and running are detected using the same algorithm, such as the algorithm described above, by choosing the allowed cadence regularity, and/or cadence frequency and acceleration ranges to cover both walking and running.

According to another embodiment, only running is determined using the algorithm described above, and if the criteria for running are not met, a different algorithm for walking is used. The walking detection algorithm may be based for example in measuring acceleration in three dimensions to provide three-dimensional acceleration data, detecting characteristic features (corresponding to wrist motions) of these acceleration data, determining correlation factors between the characteristic features in all the three dimensions. The correlation factors define three-dimensional correlation vectors, whereby the determination of whether the motion measured corresponds to walking can be evaluated based on direction and magnitude of the correlation vectors (i.e. spatial location of the dimension-specific correlation factors). The correlation factors are calculated for each characteristic feature detected such that data values at predefined points of the feature are multiplied with data values at corresponding points of a previous detected feature. The multiplication results can then be summed to obtain a correlation factor depicting correlation between the two features. The correlation factors can then be saved as a time series for further use.

According to one embodiment, the activity index represents a relative intensity of training. The higher the physical intensity of the training, the faster the activity index is increased. Higher intensity of running compared to walking is reflected in higher cadence and higher average acceleration. The processing unit is adapted to increase the activity index based on one or both of them more rapidly during running than during walking.

The activity index can be dedicated to running and/or walking only, i.e., it is not updated if any other physical activity is detected. The activity index can also be common to all activities the device is capable of detecting, i.e., is updated also in other activity monitoring modes than the running and/or walking mode.

Also other quantities than the activity index can be computed based on intermediate values of the processing, such as cadence, speed or average wrist acceleration, or the end value, i.e. the activity index. For example, cadence can be used to compute the number of steps taken by the person if multiplied by time. Similarly, speed can be used to compute the distance travelled. The activity index can be used to compute the energy consumption, the training effect, the peak training effect, or the recovery time needed.

According to one embodiment, in addition to the first automatic activity monitoring mode discussed above, there are one or more second activity monitoring modes defined in the device, for example for gym training, swimming, cycling and/or various team sports. Such second activity monitoring modes can be started and stopped through the user interface of the device. Such manually started mode may override the automatic mode, i.e., the activity index is updated using the update criteria of the second mode instead of the first mode, or instead another activity index is updated. The second activity monitoring mode(s) can use also other sensors than the built-in acceleration sensor, for example a heartbeat sensor, satellite positioning sensor, bike pod or foot pod. The other sensor(s) may be built-in or in wireless communication with the present device.

The first activity monitoring mode may be operational whenever the present device is switched on, or according to a calendar set by the user, or upon user input, to mention some examples. Even if programmed to require user input to start/stop, the first activity monitoring mode distinguishes from the one or more second activity monitoring modes in that the update criteria of the activity index are bound to the detection of walking or running, whereas in the other modes the monitoring are typically not depending on such detection, as different criteria are used. Preferably, there are at least two sports-type specific second modes that are launched through the user interface of the device by selecting the particular sports the user is going to exercise, after which all data provided by the acceleration or other sensor(s) is interpreted to belong to that sports exercise until the user terminates the mode through the user interface.

In one embodiment, all other movement activity measured by the acceleration sensor than that recorded in the first activity monitoring mode and optionally in the one or more second activity monitoring modes, are determined to be part of baseline activity, i.e. is not specifically recorded, or, if recorded, as a separate activity index different than that used in the first and/or second activity monitoring mode(s).

In one embodiment, in the automatic activity monitoring mode, if one or all of the abovementioned checks (cadence regularity and frequency and acceleration strength) fail, while the overall intensity of acceleration remains at a predefined level for a predefined period, the device suggests the user through its user interface to manually start a second activity monitoring mode corresponding to the activity taking place.

EXAMPLE

Acceleration values $a_x$, $a_y$ and $a_z$ in three orthogonal directions x, y, z are measured using acceleration sensors. The total magnitude of the acceleration vector is $a_1$:

$$a_1 = \sqrt{a_x^2 + a_y^2 + a_z^2} \qquad (1)$$

Gravity $g_0$ is subtracted from total acceleration, yielding movement-related acceleration $a_2$:

$$a_2 = a_1 - g_0 \qquad (2)$$

A plurality of movement-related acceleration values $a_2$ are measured over a time period $\Delta t$ and used to calculate average movement acceleration $a_{ave}$ $$a_{ave} = \frac{\sum a_2(t)}{\Delta t} \qquad (3)$$

Then, the average acceleration $a_{ave}$ is converted to running speed $v_{running}$ using a piecewise linear function $f_{mapping}(\ )$, also applying a cadence check function $f_{cadenceCheck}(\ )$, which checks that $a_{ave}$ and cadence detected from the acceleration signal are at allowed ranges:

$$v_{running} = f_{cadenceCheck}(\text{cadence}, a_{ave}) f_{mapping}(a_{ave}) \qquad (4)$$

The mapping function $f_{mapping}(\ )$ can have a predefined form, but its form can also be changed using reference measurements to adapt the function to individual running characteristics of the person.

Figure 4A:
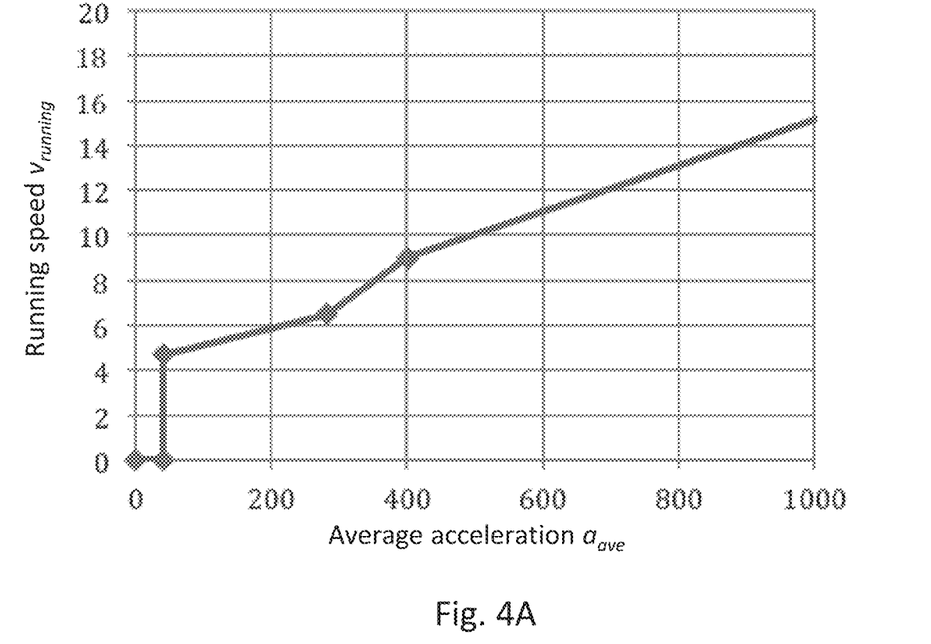
FIGS. 4A and 4B show a running speed vs. average acceleration graph and acceptable average acceleration and cadence graphs which can be used by the present device to implement robust walking and running activity determination.

According to one embodiment, the adaptation of the mapping function is carried out as an autocalibration without user involvement. Autocalibration may for example take place if the user switches on a speed measurement module such as a satellite positioning sensor or footpod sensor yielding the true speed of the person. The present device receives the speed data obtained using such sensors, and utilizes the speed information for updating the piecewise linear function to reflect the correct relation between $a_{ave}$ and the measured reference speed. The function is then saved for further speed determination as described above. The device may also itself command a speed measurement module to perform the autocalibration. FIG. 4A shows an example of a piecewise linear mapping function.

Figure 4B:
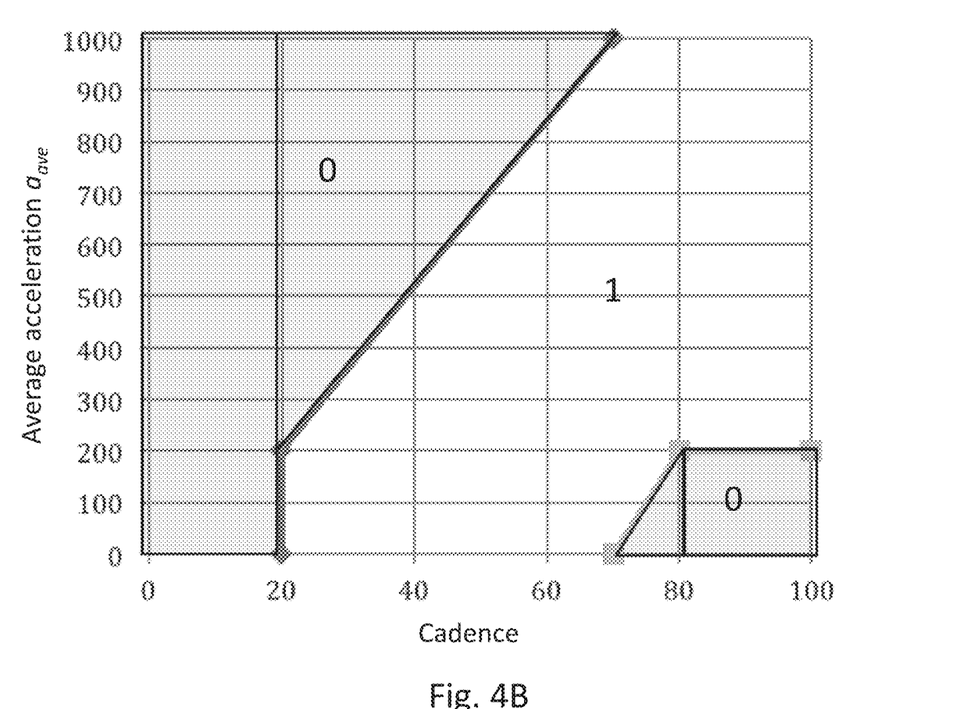

The value of the cadence check function $f_{cadenceCheck}(\ )$ is either 1 or 0, depending on whether both cadence and $a_{ave}$ are within predefined ranges or not. FIG. 4B shows an example of a cadence check function. In the central portion, if cadence and average acceleration are lying between the thick lines, the measurement can be determined to originate from running or walking, and the function takes the value 1. Outside this zone, the value is 0, rendering the value of $v_{running}$ also 0.

It has been found in practical tests, that the device and method as herein described provides results that are in good correlation with reality. Among twenty test persons, the method produced only a 5% average error in distance travelled (computed from speed), compared to a distance determined using a foot pod, even if using a predefined cadence/acceleration-to-speed conversion. The standard deviation was nearly 30%, but autocalibration of the cadence/acceleration-to-speed conversion is expected to reduce this figure significantly, because individual variations in motion trajectories are then being taken into account.

Figure 5:
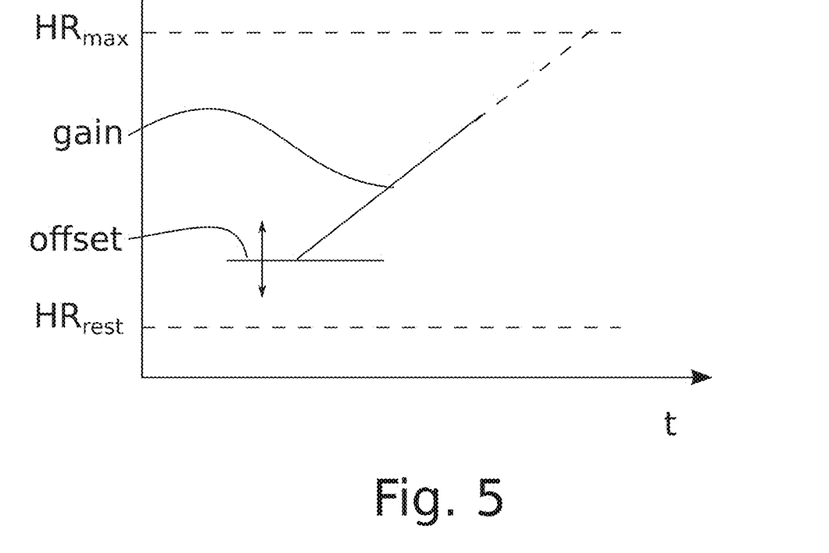
FIG. 5 shows schematically the relation between a cumulative index (offset) and a current index (gain)

In FIG. 5, a graph is shown over the general relation between exercise time t and the heart rate. $HR_{rest}$ is the pulse value of a person when at a complete rest, and $HR_{max}$ is the maximum pulse. At a certain physical condition of an individual, these pulse values are relatively stable and may serve as a basis for further calculation of various parameters, which describe the load the current exercise is imposing on the body. According to the invention, a cumulative activity parameter, the heart rate offset, is based on at least one of the following data: the predetermined pulse $HR_{rest}$, a predetermined fitness level of the person, a current recovery pulse of the person, and/or the cumulated acceleration data during the current activity. The fitness level and recovery pulse calculation may include the use of the recovery time and/or the maximum pulse $HR_{max}$ of the person, as discussed below. The offset value is stored in the memory unit. As can be seen, the offset value may go up and down depending on different phases or varying outer circumstances of the exercise or activity. One interpretation of the offset is that it is the current rest pulse, i.e. a temporary new pulse baseline, during the activity.

One usable offset value as such is the recovery time of the person, or a derivative thereof. The concept of recovery time and its measurement is the subject of the co-pending U.S. patent application Ser. No. 13/071,624, which is incorporated herein by reference in its entirety.

Recovery time describes the rest time needed for a person to fully recover from his/her current exercise. The recovery time depends on the duration of the exercise, its load and on the fitness level of the person. The recovery time can be recursively calculated on the basis of an earlier defined recovery time so that each time when the current pulse level exceeds the defined recovery pulse level, the recovery time is increased, and each time when the current pulse level is lower than or equal to the defined recovery pulse value, the recovery time is reduced. The recovery time may also be calculated on the basis of the so-called effective exercise time, the effective exercise time being calculated from the actual pulse frequency and the maximum performance pulse, the maximum performance pulse preferably being chosen depending on the type of the discipline of the athlete.

In practice, the recovery time can be estimated by calculating the "effective exercise" time which depends on the duration of the exercise and its load.

An effective exercise time addition $\Delta d_{eff}$ is computed by means of a first conversion function $f1$. For running, the conversion function can be e.g. of the following form:

$$\Delta d_{eff} = f1(HR, HR_{rec}, HR_{max}) = (\exp(2*(HR-HR_{rec})/(HR_{max}-HR_{rec}))-1)*C, \quad (5)$$

where $C = C(HR, HR_{rest}, HR_{max}) = 0.00057*hrr*hrr - 0.11360*hrr + 7.34503$ The exact form of the function depends on the sports. In the above it has been supposed that the measured pulse HR is higher than the calculated recovery pulse $HR_{rec}$. The constant coefficients shown in the formula are examples only. $HR_{max}$ is here the maximum theoretical performance pulse during the exercise. hrr is the percentage of the pulse reserve available, and may be defined as $$hrr = (HR - HR_{rest})*100\%/(HR_{max} - HR_{rest}) \quad (6)$$

The function $f1$ above has been formed using the principles laid out in U.S. patent application Ser. No. 13/071,624 as identified above.

The effective exercise time is a cumulative sum of a previously calculated effective exercise time and the $\Delta d_{eff}$.

Figure 8:
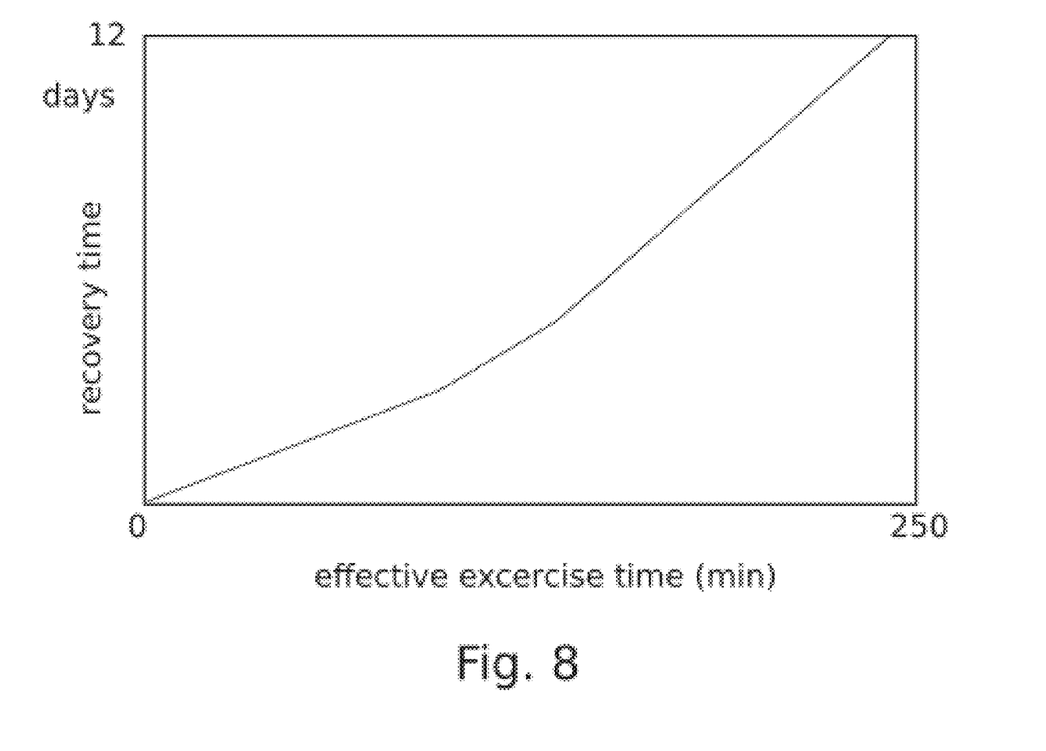
FIG. 8 shows a relation between the training time and the recovery time.

The effective exercise time can be converted to recovery time by means of a second conversion function $f2$. For example, FIG. 8 shows an example of such a conversion function. In running the conversion function $f2$ may be formed by tabulating the recovery requirements from maximal performances as a function of distance corresponding to the performance. It has been suggested that in competitive sports, for a performance of 8 km the necessary rest is one week, for 16 km two weeks and for half marathon a month.

Thus, the relation is shown in FIG. 8 depends on the sport. The fitness level of the person need to be taken into account, as it has an effect on the ability of the body to recover from an exceptional condition caused by physical exertion. For example, at least one of the following parameters may be stored in the memory unit of an inventive monitoring device for computing and updating the offset value: age of the person, sex of the person, mass of the person, fitness index of the person, maximum oxygen intake value ($VO_{2,max}$) of the person.

According to one embodiment, when the pulse exceeds the maximum performance pulse, the recovery time is increased more than with the pulse being between the recovery pulse and the maximum performance pulse. Such behavior can be modeled, e.g. with a linear function.

Further, returning to FIG. 5, a second activity parameter called the current activity gain value, is also computed. The gain value is based on current acceleration data and heart rate data, and is stored in the memory unit. As can be seen from FIG. 5, the gain is a sloped curve, which varies from one individual to another and also from one activity to another. Generally, the gain describes the relation $\Delta HR/\Delta acc$, where $\Delta acc$ is accelerometer data describing the acceleration changes in a certain time interval, and $\Delta HR$ is the corresponding change in the heart rate during the same time interval. $\Delta acc$ may be the change in the average acceleration, computed for example according to formula (3) above. Correspondingly, $\Delta HR$ may be corresponding change in the average heart rate. In practice, it is feasible to determine in the first operating mode, for example during periods of 10 seconds, the average acceleration values and heart beat rate values. The average data between two consecutive 10 second periods may then be used to compute variables $\Delta HR$ and $\Delta acc$, which are the differences of the two average heart beat rate and acceleration values, respectively. A current activity gain value may then be computed based on the ratio $\Delta HR/\Delta acc$.

Alternatively or in addition, in some embodiments, the periodic motions made by the user may be detected from measured acceleration data, and the frequency of the motions may be determined. A current activity gain value may then be computed only if the frequency of the periodic motions is at a predefined frequency range.

Different sports need different motion parameters, like acceleration, cadence, periodicity etc., in order to correctly capture the physical activity and the load it represents. The sports selection may be made manually by the user via a user interface of the device (see e.g. item 73 in FIG. 7), or the sports discipline may be automatically detected by observing the activity with one or several acceleration sensors worn by the user.

Thus, in a steady tempo performance like in walking and running, which has been going on for a while, the gain is steady when the body metabolism has settled to a certain level. In the very beginning of an activity, the gain is low as the acceleration data is high and the heart rate reacts slower, but grows as the acceleration data becomes levelled and the pulse increases.

Regarding FIG. 5, it should be noted that both the offset and the gain may be dimensionless indexes. They are placed in a coordinate system of time vs. heart rate only for illustrative purposes, which show their internal relations in their framework of pulse monitoring.

In the present invention, a monitoring device for monitoring the physical activity of a person is switched between a first operating mode where actual measurement of acceleration and physiological variables such as the heart rate is conducted, and a second operating mode where measurement is discontinued and the relevant parameters of interest are estimated, by augmenting the measured physiological variable with acceleration data. The measurements may be performed with predefined intervals, for example with a second operating mode lasting at least 5 times longer than the first operating mode.

Figure 6:
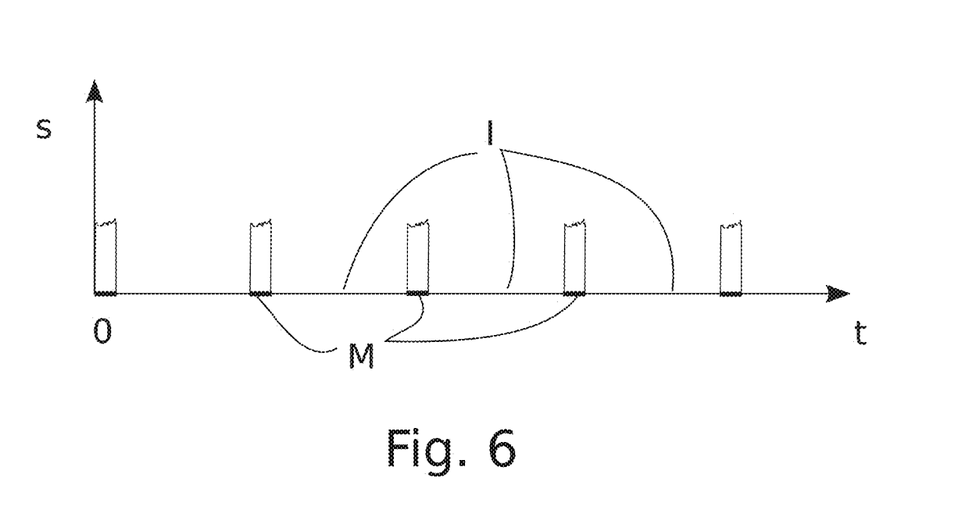
FIG. 6 shows schematically an exemplary measuring scheme according to the invention.

In FIG. 6 is schematically shown the measurement time intervals "M" of the first operating mode along the horizontal axis "t". The processing unit of the monitoring device is during the "M" periods reading data from first and second sensors (signals "s" on the y-axis). Predefined intervals "I" represent the second operating mode, where the processing unit is computing estimates of the offset and gain values. These estimates may be produced by a linear modelling of the actually measured results, i.e. by linear extrapolation of actual measured values during the previous first operating mode. Each sport discipline may need different modelling.

In some embodiments, the data processing unit may be configured to determine an average acceleration value from acceleration data measured during the first operating mode, to determine whether said average acceleration is within a predefined acceleration range, and to filter acceleration data by computing a new current activity gain only if the average acceleration is within the predefined acceleration range.

Figure 7:
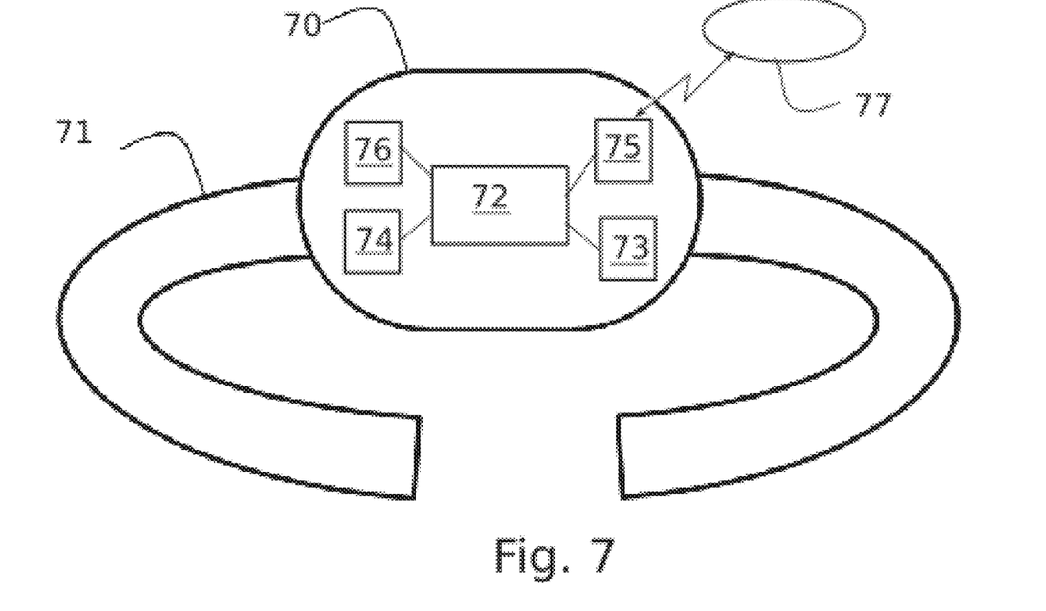
FIG. 7 shows a device according to one embodiment.

FIG. 7 shows a device according to one embodiment the invention and similar to the one in FIG. 1. The device comprises a main unit 70 and a wristband 71 attached to the main unit 70. The main unit comprises a data processing unit 72 and an acceleration sensor 74, memory unit 76 and user interface unit 73, all functionally connected to the data processing unit 72. The device also comprises a heart rate sensor 75, which may include a wireless interface to external sensors 77, such as an accelerometer placed on the body or in a garment of a user, or a heart rate sensor/transmitter to be worn around the chest.

Wireless communication of data between wireless interfaces and devices such as 75 and 77 in a multi-device environment may use a wireless radio-frequency transmitter-receiver or transceiver-transceiver pair. The wireless communication protocol can be one used for communication between computers, and/or between any remote sensors, such as a Bluetooth LE or the proprietary ANT+ protocol. These are using direct-sequence spread spectrum (DSSS) modulation techniques and an adaptive isochronous network configuration, respectively. Enabling descriptions of necessary hardware for various implementations for wireless links are available e.g. from the Texas Instrument®'s handbook "Wireless Connectivity" which includes IC circuits and related hardware configurations for protocols working in sub-1- and 2.4-GHz frequency bands, such as ANT™, Bluetooth®, Bluetooth® low energy, RFID/NFC, PurePath™ Wireless audio, ZigBee®, IEEE 802.15.4, ZigBee RF4CE, 6LoWPAN, Wi-Fi®.

The data processing unit 72 can comprise a microcontroller, optionally with the memory unit 76 built therein. The data processing unit 72 is capable of running a program code including instructions necessary for the device to operate according to the invention, and FIG. 7 illustrates an example apparatus capable of supporting at least some embodiments of the present invention. Illustrated is device 70, which comprise a processing unit 72, which may comprise, for example, a single- or multi-core processor wherein a single-core processor comprises one processing core and a multi-core processor comprises more than one processing core. Processing unit 72 may comprise more than one processor. A processing core may comprise, for example, a Cortex-A8 processing core manufactured by ARM Holdings or a Steamroller processing core produced by Advanced Micro Devices Corporation. Processing unit 72 may comprise at least one Qualcomm Snapdragon and/or Intel Atom processor. Processing unit 72 may comprise at least one application-specific integrated circuit, ASIC. Processing unit 72 may comprise at least one field-programmable gate array, FPGA. Processing unit 72 may be means for performing method steps in device 70, and it may be configured, at least in part by computer instructions, to perform actions.

Memory unit 76 may comprise random-access memory and/or permanent memory. Memory 76 may comprise at least one RAM chip. Memory 76 may comprise solid-state, magnetic, optical and/or holographic memory, for example. Memory 76 may be at least in part accessible to processing unit 72. Memory 76 may be at least in part comprised in processing unit 72. Memory 76 may be means for storing information. Memory 76 may comprise computer instructions that processing unit 72 is configured to execute. When computer instructions configured to cause processing unit 72 to perform certain actions are stored in memory 76, and device 70 overall is configured to run under the direction of processing unit 72 using computer instructions from memory 76, processing unit 72 and/or its at least one processing core may be considered to be configured to perform said certain actions. Memory 76 may be at least in part comprised in processing unit 72. Memory 76 may be at least in part external to device 70 but accessible to device 70.

The acceleration sensor 74 can comprise a one-, two- or most preferably a three-dimensional accelerometer, which are well known in the art. The heart rate sensor 75 can comprise EKG electrodes or optical means for registering the blood pulses in the veins of the user. Sensor 75 may be an optical heart rate sensor. Because optical sensors may sometimes have difficulties in detecting the pulse, the inventive monitoring device may be maintained in the second operating mode extending the predefined interval, if a heart rate signal from the optical sensor is unavailable. The device may be configured then to merely continue calculating and displaying an estimate, until an acceptable measured pulse rate values are again obtained.

The user interface unit 73 comprises the necessary means for the user to interact with the program code of the device, e.g. switch on and off the device, to change mode of activity monitoring mode of the device or to input personal parameters (input means) and to visually inspect the cumulative and/or current activity index (output means). The input means may comprise one or more buttons or a touchscreen. The output means comprise a user-readable display unit used to display, for example, the measured heart rate values during the first mode of operation of the monitoring device, and the estimated and augmented heart rate values during the second mode of operation of said monitoring device.

The processing unit 72 may according to the invention be configured to display the current estimated heart beat rate value, which is based on the offset value and the gain value augmented with acceleration data as described above, during the second operating mode on the display unit 73. Alternatively or in addition, the processing unit may be configured to store in the memory unit 76 the estimated heart beat rate values, to show their values on a graph versus time, for example.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures or characteristics may be combined in any suitable manner in one or more embodiments. In the description numerous specific details are provided to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A device for monitoring physical activity of a person, comprising
   at least one first sensor for measuring acceleration data relating to movements of said person,
   at least one second sensor for measuring heart rate data corresponding to the heart beat rate of said person,
   said first and second sensors being connected to a data processing unit comprising at least one processing core, at least one memory unit including computer program code, the at least one memory unit and the computer program code being configured to, with the at least one processing core, cause the device to operate in a first mode when data is read from said first and second sensors and in a second mode when data is not read from the said first sensor or the said second sensor, and
   where the data processing unit in said first operating mode:
     determines at least first and second average acceleration values from measured acceleration data,
     determines at least first and second average heart rate values from measured heart beat data,
     cumulatively computes and updates a heart rate offset value based on at least one of the following data: a predetermined pulse of the person at rest, a predetermined fitness level of the person, a current recovery pulse of the person, and/or the cumulated acceleration data during activity,
     computes a current activity gain value based on the average acceleration values and the average heart beat rate values, and wherein
   said data processing unit being further configured to;
     compute an estimate of the current heart beat rate based on said offset value and said activity gain value during said second operating mode,
     determine at least first and second average acceleration values from acceleration data measured during at least two time periods during said first operating mode,
     determine at least first and second average heart beat rate values from heart rate beat data measured during at least two time periods during said first operating mode, and
     compute a new current activity gain value based on the ratio between the differences $\Delta HR/\Delta acc$ of said at least two average heart beat rate and acceleration values.

2. The device according to claim 1, wherein the processing unit is configured to calculate the heart beat rate offset value as a parameter corresponding to a recovery time of the user, said recovery time being computed as a function of the duration of the current activity, a predetermined or estimated heart beat rate or pulse value characteristic of the user at rest, and the current heart rate.

3. The device according to claim 1, wherein the processing unit is configured to calculate the current activity gain value as a parameter corresponding to the ratio of differences between said heart beat rate data and said acceleration data.

4. The device according to claim 1, wherein the processing unit is configured to display the current estimated heart beat rate value based on said offset value and said activity gain value during said second operating mode on a user-readable a display unit of said device.

5. The device according to claim 1, wherein the processing unit is configured to store in said at least one memory unit the estimated heart beat rate values based on said offset value and said activity gain value during said second operating mode.

6. The device according to claim 1, wherein the processing unit is configured to switch between said first and second operating modes with predefined intervals.

7. The device according to claim 6, wherein the processing unit is operating in said second operating mode at least 5 times longer than in said first operating mode.

8. The device according to claim 1, wherein the data processing unit is configured to:
detect periodic motions from measured acceleration data,
determine frequency of the periodic motions,
determine whether the frequency of the periodic motions is at a predefined frequency range, and to
compute a new current activity gain value using said frequency of periodic motions if the frequency of the periodic motions is at said predefined frequency range.

9. The device according to claim 1, wherein the data processing unit is configured to:
determine an average acceleration value from acceleration data measured during said first operating mode,
determine whether said average acceleration is within a predefined acceleration range,
compute a new current activity gain value using said average acceleration if the average acceleration is within said predefined acceleration range.

10. The device according to claim 1, wherein the processing unit is configured to compute estimates of said offset value and said activity gain value during said second operating mode by linear extrapolation of earlier measured values during said first operating mode.

11. The device according to claim 1, wherein the processing unit is configured to use at least one of the following parameters stored in said memory unit for computing and updating said offset value: age of the person, sex of the person, mass of the person, fitness index of the person, maximum oxygen intake value ($VO_{2,max}$) of the person.

12. The device according to claim 1, wherein the device is a wristop computer.

13. The device according to claim 1, wherein the said at least one second sensor comprises an optical heart rate sensor.

14. The device according to claim 1, the device being a wearable computer further comprising at least one transceiver.

15. The device according to claim 1, wherein the data processing unit is configured to:
determine an average acceleration value from acceleration data measured during said first operating mode,
determine whether said average acceleration is within a predefined acceleration range,
compute a new current activity gain value using said average acceleration if the average acceleration is within said predefined acceleration range.

16. The device according to claim 1, wherein said data processing unit is configured to automatically detect a sports discipline by observing the activity of the user with the at least one first sensor.

17. A method for monitoring physical activity of a person by operating a monitoring device in a first operating mode and in a second operating mode, the method comprising further steps of:
measuring in said first operating mode at least first and second average acceleration data relating to movements of said person with a first sensor, said acceleration data being transmitted to a processing unit,
measuring in said first operating mode at least first and second average heart beat rate data corresponding to the heart beat rate of said person with a second sensor, said heart beat rate data being transmitted to the processing unit,
computing and updating a cumulative heart rate offset value based on at least one of the following data: a predetermined pulse of the person at rest, a predetermined fitness level of the person, a current recovery pulse of the person, and/or the cumulated acceleration data during activity,
computing a current activity gain value based on measured first and second average acceleration data and measured first and second average heart beat rate data,
computing an estimate of the current heart beat rate based on said offset value and said activity gain value during said second operating mode,
determining at least first and second average acceleration values from acceleration data measured during at least two time periods during said first operating mode,
determining at least first and second average heart beat rate values from heart rate beat data measured during at least two time periods during said first operating mode, and
compute a new current activity gain value based on the ratio between the differences $\Delta HR/\Delta acc$ of said at least two average heart beat rate and acceleration values.

18. The method according to claim 17, wherein the heart beat rate offset value is calculated as a parameter corresponding to a recovery time of the user, said recovery time being computed as a function of the duration of the current activity, a predetermined or estimated heart beat rate or pulse value characteristic of the user at rest, and the current heart rate.

19. The method according to claim 17, wherein the current activity gain value is calculated as a parameter corresponding to the ratio of the differences between said heart beat rate data and said acceleration data.

20. The method according to claim 17, wherein the current estimated heart beat rate value based on said offset value and said activity gain value during said second operating mode is displayed on a user-readable display unit of said monitoring device.

21. The method according to claim 17, wherein the estimated heart beat rate values based on said offset value and said activity gain value during said second operating mode store is stored in a memory unit of said monitoring device.

22. The method according to claim 17, wherein said monitoring device is switched between said first operating mode and said second operating mode with predefined intervals.

23. The method according to claim 22, wherein said monitoring device is operating in said second operating mode at least 5 times longer than in said first operating mode.

24. The method according to claim 17, comprising the further steps of:
detecting periodic motions from measured acceleration data,
determining a frequency of the periodic motions,
determining whether the frequency of the periodic motions is at a predefined frequency range, and
computing a new current activity gain value using said frequency of periodic motions if the frequency of the periodic motions is at said predefined frequency range.

25. The method according to claim 17, comprising the steps of:
- determining an average acceleration value from acceleration data measured during said first operating mode,
- determining whether said average acceleration is within a predefined acceleration range,
- computing a new current activity gain value using said average acceleration if the average acceleration is within said predefined acceleration range.

26. The method according to claim 17, comprising the step of computing estimates of said offset value and said activity gain value during said second operating mode by linear extrapolation of earlier measured values during said first operating mode.

27. The method device according to claim 17, wherein at least one of the following parameters stored in said memory unit is used for computing and updating said offset value: age of the person, sex of the person, mass of the person, fitness index of the person, maximum oxygen intake value ($VO_{2,max}$) of the person.

28. The method according to claim 17, wherein the heart rate is measured by optical heart rate sensors.

29. The method according to claim 27, wherein said at least one second sensor measuring the heart rate comprise an optical heart rate sensor, and said monitoring device is maintained in said second operating mode over said predefined interval, if a heart rate signal from said optical sensor is unavailable.

30. The method according to claim 17, wherein wireless communication is used to transfer data between said sensors and said monitoring device.

31. A computer program product stored on a computer readable non-transitory storage medium in a monitoring device for monitoring physical activity of a person, said product comprising a computer readable program code causing said monitoring device to operate in a first operating mode and in a second operating mode, wherein:
- in said first operating mode acceleration data relating to movements of said person is measured with a first sensor and transmitted to a processing unit,
- in said first operating mode heart rate data corresponding to the heart beat rate of said person is measured with a second sensor and transmitted to the processing unit,
- a cumulative heart rate offset value is computed and updated based on at least one of the following data: a predetermined pulse of the person at rest, a predetermined fitness level of the person, a current recovery pulse of the person, and/or the cumulated acceleration data during activity,
- a current activity gain value is computed based on an average of the measured acceleration data and an average of the measured heart beat rate data, and
- an estimate of the current heart beat rate is computed based on said offset value and said activity gain value during said second operating mode said activity gain value during said second operating mode,
- at least first and second average acceleration values from acceleration data measured during at least two time periods during said first operating mode,
- at least first and second average heart beat rate values from heart rate beat data measured during at least two time periods during said first operating mode, and
- a new current activity gain value based on the ratio between the differences $\Delta HR/\Delta acc$ of said at least two average heart beat rate and acceleration values.

* * * * *